United States Patent [19]

Rice et al.

[11] Patent Number: 4,544,629
[45] Date of Patent: Oct. 1, 1985

[54] RECEPTOR-BASED HISTAMINE ASSAY

[75] Inventors: Thomas K. Rice, White Bear Lake; Therese A. Senta, Minneapolis, both of Minn.

[73] Assignee: Minnesota Mining and Manufacturing Company, St. Paul, Minn.

[21] Appl. No.: 443,155

[22] Filed: Nov. 19, 1982

[51] Int. Cl.$^4$ .................. G01N 33/54; C12Q 1/42; C12Q 1/28; C12Q 5/02; C12Q 9/96
[52] U.S. Cl. .......................... 435/7; 435/21; 435/241; 435/188; 435/810; 435/28; 436/503; 436/518; 436/519; 436/536; 436/808; 436/811
[58] Field of Search .................. 435/4, 7, 21, 25, 188, 435/240, 241, 810, 28; 436/503, 518, 519, 528, 536, 537, 807, 808, 811; 260/112 R, 112 B

[56] References Cited

U.S. PATENT DOCUMENTS 4,299,813 11/1981 Snyder .................. 436/808
4,327,073 4/1982 Huang .................. 435/7

FOREIGN PATENT DOCUMENTS 53-75323 7/1978 Japan .................. 436/503

OTHER PUBLICATIONS

Smythies et al., *Receptors in Pharmacology*, Marcel Dekker, Inc., N.Y., pp. 2, 7 and 123-150 (1978).
Simon, *Receptors as Supramolecular Entities*, Proc. Biannual Capo Boi Conf., Cagliari, Italy, Jun. 7-10, 1981, Pergamon Press, N.Y., 301, 314, 315 (1983).
Stoner, "Enzyme Affinity Assay-A New Method for the Quantitation of Histamine", Ph.D. Dissertation, University Microfilms International, Ann Arbor, Mich. (1981).
Stoner, Dissertation Abstracts International, 42(8), 3277b (Feb. 1982).
Wisdom, Clin. Chem., 22(8), 1243-1255 (1976).
Rocklin et al., Chemical Abstracts, 88: 168394x, (1978).

*Primary Examiner*—Esther M. Kepplinger
*Attorney, Agent, or Firm*—Donald M. Sell; James A. Smith; Lorraine R. Sherman

[57] ABSTRACT

A receptor-based clinical or research competitive inhibition assay method for determining histamine in body or laboratory fluids is disclosed. A kit for carrying out the method is also described comprising an amount of histamine receptors sufficient to provide an excess of receptors for binding with the amount of histamine in the sample to be assayed, and an amount of a histamine-indicator conjugate sufficient to react with the resulting unbound histamine receptors present after reaction of the histamine sample with the histamine receptors.

16 Claims, No Drawings

RECEPTOR-BASED HISTAMINE ASSAY

TECHNICAL FIELD

The present invention relates to a method of assaying histamine. More particularly, it relates to a receptor-based competitive inhibition assay for determining histamine in body or laboratory fluids. In another aspect, it relates to a kit useful in the method of the present invention. In a further aspect, it relates to a novel histamine-indicator conjugate for use in the method of the present invention.

BACKGROUND ART

Histamine is found in many biological systems and plays a major role in the generation of symptoms of allergic and inflammatory disease. It is known that histamine is involved in the immune response, in secretion of gastric acid, and in the functioning of the nervous system. Histamine is released from granules contained within tissue mast cells and circulating basophils. The release of histamine is often a reaction to the association of an antibody on the surface of such a cell with an allergen. Released histamine interacts with many body tissues to induce changes which are symptomatic of several diseases. It is well established that the amount of histamine released is an excellent indicator of the presence and severity of certain diseases. For example, the amount of histamine release provoked by an allergen is an excellent indicator of the degree of allergic sensitivity to the allergen. Measurement of the amount of histamine released in response to challenge by an allergen is not commonly used as a diagnostic method because of the inadequacies of currently available methods of histamine quantification.

There is a wide range of methods available in the prior art for the quantitative measurement of histamine. However, none of the available methods are adequate for routine use in a clinical laboratory. The most widely used assays are variations of an ortho-phthalaldehyde conjugation assay. In this method histamine in a body fluid such as blood or urine is separated from other biological amines by a series of organic-inorganic phase extractions with concomitant shifts in pH. The isolated histamine is then reacted with ortho-phthalaldehyde to provide a fluorescent product which is quantified. This procedure is labor-intensive, and when automated, requires major capital investment and dedication of capital equipment.

An alternative histamine assay is an enzymatic isotopic assay wherein a radioisotope tag is attached to histamine by radioisotope-labeled adenosylmethionine in the presence of methyltransferase. This assay also requires an extraction procedure. It is time consuming, labor-intensive, and presents the usual problems associated with the use of radioisotopes.

Less commonly used histamine assay methods include high pressure liquid chromatography of fluoresceamine-conjugated histamine, various gas chromatographic assays, and a thin layer chromatographic assay. While these methods are more or less useful in research laboratories, none combines the features necessary for a clinical laboratory assay method, such as accuracy, speed, ease of operation, low cost, and high volume.

Receptor-based assays are known in the art. U.S. Pat. No. 3,817,837 relates to an assay method for determining the presence of a ligand which may be histamine. The ligand is bound to an enzyme and the enzyme-bound ligand is required to undergo a substantial reduction in enzymatic activity when binding to a receptor. In contrast, the preferred histamine-indicator conjugate of the present invention maintains its activity or even undergoes stimulation of activity when bound to a receptor.

The only commercially available receptor-based assay is believed to be Biocept-G ® (Wampole Laboratories, Dist. Div. of Carter-Wallace, Inc., Cranbury, N.J.). Biocept-G ® is a pregnancy test based on the specific binding of human chorionic gonadotropin (HCG) in blood serum to preparations of plasma membranes from animal cells such as those of rat testes or bovine corpora lutea.

SUMMARY OF THE INVENTION

Briefly, the present invention provides a competitive inhibition method for quantitative measurement of histamine in a liquid test sample using histamine receptors and a histamine-indicator conjugate, the method comprising the steps:

1. contacting a measured amount of a test sample with an excess of the histamine receptors,
2. incubating and reacting the test sample with the histamine receptors, which reaction leaves unbound histamine receptors available for further bonding,
3. contacting an amount of a histamine-indicator conjugate with the bound and unbound histamine receptors sufficient to bind said histamine-indicator conjugate to all unbound histamine receptors,
4. incubating and reacting the histamine-indicator conjugate with the unbound histamine receptors,
5. removing unbound histamine-indicator conjugate if necessary to measure the amount of histamine-indicator conjugate bound to the histamine receptors,
6. measuring the amount of histamine-indicator conjugate bound to the histamine receptors, and
7. determining the amount of histamine in the test sample by comparison with a standard curve.

Alternatively, the histamine and the histamine-indicator conjugate can be simultaneously incubated with the histamine receptors.

In one embodiment, an enzyme stimulation assay method, the above-mentioned method is adapted to incorporate as the histamine-indicator conjugate a novel histamine-enzyme conjugate, e.g., histamine-alkaline phosphatase, which conjugate when linked to a receptor through the histamine portion provides a stimulation effect to the enzyme.

The enzyme stimulation assay method of the present invention differs from the method presented immediately above in that the receptors need not be attached to a solid substrate but may be free-floating, i.e., it can be a homogeneous assay system. In such a case, the method provides an advantage by eliminating step 5, the removal step for unreacted histamine-indicator conjugate.

The above-mentioned method can be utilized with components present in kit form, the kit being particularly useful for determination of allergen sensitivity.

As used in the present application:

"histamine receptor" means a biochemical entity which is a naturally-occurring structure on the outside surface of various types of cells, which receptor specifically binds histamine. The biochemical entity is partially protein in composition and excludes antibodies and lectins;

"quantitative" means that as little as 0.1 nanogram of histamine per milliliter of sample, such as blood, urine, saliva, tissue culture fluid, cerebral spinal fluid, or cells in a buffered solution, can be reliably measured;

"competitive histamine inhibition assay" means that free histamine competes with labeled histamine for a histamine receptor in a quantitative determination of histamine in a clinical or laboratory test;

"labeled" means anything detectable by physical or chemical means, for example, radioisotope, enzyme, fluorescent compound, dye, or a substance that causes paramagnetic resonance;

"heterogeneous assay system" means a system wherein the receptors are attached to a substrate;

"homogeneous assay system" means a system wherein all receptors are free floating and are not attached to a substrate;

"stimulation effect" means increased activity of an enzyme when it is linked with histamine and bound, through histamine, to a receptor.

DETAILED DESCRIPTION

The present invention provides a method for determining the amount of histamine in a liquid test sample using histamine receptors and a histamine-indicator conjugate comprising the steps:

1. contacting a measured amount of a liquid test sample with an excess of histamine receptors,
2. incubating and reacting said test sample with said histamine receptors, which reaction leaves unbound histamine receptors available for further bonding,
3. contacting an amount of histamine-indicator conjugate with the bound and unbound histamine receptors sufficient to bind said conjugate to unbound histamine receptors,
4. incubating and reacting said histamine-indicator conjugate with unbound histamine receptors,
5. removing unbound histamine-indicator conjugate if necessary to measure the amount of histamine-indicator conjugate bound to the histamine receptors,
6. measuring the amount of histamine-indicator conjugate bound to said histamine receptors, and
7. determining the amount of histamine in said test sample by comparison with a standard curve.

In the present invention, receptors for histamine obtained from any source may be used. Receptors from animal sources, specifically from mammalian sources, are preferred. Human and animal sources, e.g., mouse, rat, guinea pig, and rabbit sources, are useful and readily available. Histamine receptors are found on the outside surface of mast cells, certain smooth muscle cells, and certain nerve cells. Preferably the source of histamine receptors are lymphoid cells in a culture such as T or B lymphocytes. More preferably, the source is a lymphoblastoid cell line, and even more preferably, the lymphoblastoid cell line which can be grown in a Spinner flask suspension culture.

Histamine receptors are removed from their source by prolonged incubation in an aqueous solvent, such as phosphate buffered saline, saline, tris(hydroxymethyl)aminomethane, or any other aqueous isotonic solvent. When cell death occurs, the receptors are shed into the solvent. Alternatively, the cells may be subjected to thermal shocking at about 46° C. for a minimum of 45 minutes, in similar aqueous solvents, until the receptors are shed.

The histamine receptors used in the assay method of the present invention may be present on or bound to fresh or preserved cells, incorporated into the outer surface of a liposome vesicle, free in solution, bound to solid particles, adhered to a continuous solid phase, or adhered to the surface of an emulsion.

When the histamine receptors are in solution, the solution may be a crude one obtained by separating receptors shed by a cell, e.g., after cell death or after thermal shocking, or it may be a more purified solution wherein the receptors have been purified or concentrated, e.g., by chromatography, on molecular sieves, or by gel exclusion or affinity chromatography.

Suitable solid phase supports useful for affixing histamine receptors include polystyrene, glass, nylon, polypropylene, albumin beads, latex beads, and liposomes, and is preferably a 96-well polystyrene microtiter plate.

When the receptors are attached to solid supports, the attachment is accomplished by a variety of procedures, many of which are well known in the art, including direct attachment of a protein entity to a treated or untreated solid surface or covalent attachment to a surface. Treated solid surfaces may be either chemically or physically treated (including corona discharge activation of a solid surface and treatment with the dimethylamine adduct of epoxidized polybutadiene as disclosed in U.S. Pat. No. 4,210,722). Chemical covalent attachment may include crosslinking or simple linking by bifunctional agents which may be homobifunctional (e.g., glutaraldehyde) or heterobifunctional (e.g., carbodiimide, cyanogen bromide, and trinitrobenzene sulfonate) as is known to those skilled in the art.

Preferably, the assay of the invention and particularly the articles or kits of the invention use histamine receptors affixed to a solid support.

Generally, for use as a clinical diagnostic assay of allergic susceptibility the sample to be assayed for histamine is a sample of blood or other source of basophils or mast cells. The sample is treated with an allergen to cause the release of histamine from histamine-containing cells such as basophils and/or mast cells. The amount of allergen added will generally be a predetermined amount of a typical allergen for which it is desired to measure the sensitivity of a subject. Examples of allergens which could be used are almost unlimited, since individual sensitivity of subjects to allergens varies widely, as is well known in the art. Typically, these allergens would be plant-originated, such as pollens; animal originated such as hair, fur, dander, saliva-containing serum proteins; or a variety of chemical substances, both organic and inorganic, such as smoke, house dust, foods, drugs, or industrial chemicals. Extracts of many of the above substances are allergens. In some cases the assay could be adapted to measure non-specific stimulation, e.g., by radio contrast agents such as Hypaque®, Winthrop Laboratories, New York, N.Y.

An excess amount of histamine receptors over that reasonably expected to bind the histamine in the test sample is present, so as to ensure available binding sites for the histamine-indicator molecules to be subsequently added. Excess receptors are insured by previously established standard curves. Histamine samples are adjusted by dilution such that the amount of histamine falls within the detectable limits of the standard curve. Preferably, more than 5 percent, but less than 95 percent, of the histamine receptors become bound with free histamine from a sample.

The reaction of free histamine with a receptor may be permitted to proceed at ambient temperature or, alternatively, the reaction rate can be reduced or increased by varying the temperature. Incubation of the reaction can be carried out at or near normal body temperatures to simulate the body environment. The time of incubation required is relatively short, although it may vary somewhat depending upon the allergens and receptors selected. The time will generally be one hour or less and preferably 15 minutes or less.

The histamine-indicator useful in the method of the present invention may be a histamine-fluorescent tag, radio-labeled histamine, histamine-dye, or preferably, a histamine-enzyme conjugate. The histamine-indicator conjugate may be added to the test sample/receptor mixture or optionally, the product of step 2 may be separated or purified before the histamine-indicator conjugate is added. For example, if the receptors are bound to a solid support, the support might be removed from a solution or suspension of allergen or biological fluid or alternatively the solution of allergen and biological fluid may be flushed away from the solid support.

Step 3 generally involves contacting a histamine-indicator conjugate with the receptors. If the receptors are already bound to histamine, reaction with the histamine-indicator conjugate is blocked. Since an excess of receptors are required and planned for in the method, the excess receptors are reacted with the histamine portion of the histamine-indicator conjugate. Preferably, less than 95 percent and more than 5 percent of the receptors are unbound and react with the histamine-indicator conjugate. This reaction is again ordinarily carried out by incubation at or near normal body temperatures to simulate the natural environment. The time of incubation will ordinarily be one hour or less, and preferably 15 minutes or less.

In the method of invention, the histamine-indicator preferably is a histamine-enzyme conjugate and can be chosen from a wide variety of known or easily prepared conjugates. The enzymes are preferably commercially available or inexpensive to prepare and isolate, have good stability, high levels of activity, and other obvious properties necessary for use in a commercial laboratory test.

Suitable enzymes are those which react with a readily available substrate to produce a product which is detectable and readily determined by available analytical methods and include alkaline phosphatase, horseradish peroxidase, and others that fulfill the above criteria and in addition have a high turnover rate (rate of product formation), are stable and economical to produce.

Preferred enzymes for the histamine-enzyme conjugate are alkaline phosphatase and horseradish peroxidase. Alkaline phosphatase is suitable because it is readily conjugated by reaction with 1-ethyl-3-(3-dimethylaminopropyl)carbodiimide-histamine. 1-Ethyl-3-(3-dimethylaminopropyl)carbodiimide is added to an equimolar amount of histamine to provide virtually 100% yield of the conjugate of histamine and the carbodiimide. Addition of an equimolar amount of the alkaline phosphatase provides the histamine-enzyme conjugate in a 1:1 mole ratio. The conjugate may optionally (and preferably) be purified, e.g. by chromatography on Sephadex ® G-200 (a dextran gel available from Pharmacia, Inc.). Horseradish peroxidase, is conjugated by coreaction with glutaraldehyde and histamine, in a similar manner.

The receptors are partially reacted in step 2 with histamine to be measured, e.g., histamine released by the cells of a sample in response to challenge by an allergen. Then, the remainder of unreacted receptors are completely reacted by adding excess histamine-indicator conjugate. After reaction of the histamine indicator with unbound histamine receptors, the receptor-containing sample contains completely reacted histamine receptors. Subsequently, in a heterogeneous assay system, the unreacted excess histamine-indicator conjugate is washed away using a suitable solvent, generally phosphate-buffered saline solution. Then the amount of indicator present is determined. For example, if the indicator is an enzyme, a substrate which the enzyme will react with or on is added and allowed to react. For example, with alkaline phosphatase the substrate may be p-nitrophenyl phosphate or umbelliferone phosphate; with horseradish peroxidase the substrate may be o-phenylenediamine plus hydrogen peroxide or aminoantipyrine plus hydrogen peroxide. The enzyme and substrate are chosen so that the product of their reaction is readily detectable. For example, the substrate to be reacted with the alkaline phosphatase-histamine conjugate can be para-nitrophenyl phosphate. The product of the reaction, p-nitrophenol, is a yellow-colored compound readily detected visually or by a spectrophotometer. After a specific amount of reaction time, the enzyme-substrate reaction is quenched, in this case with mild base, e.g., 1N aqueous sodium hydroxide. The color produced is measured quantitatively by a spectrophotometer. The amount of enzyme present is determined by comparison with, e.g., a graphic curve or a computer generated analysis with known amounts of enzyme and substrate.

Other indicators which are useful are also readily detected by known standard methods. Histamine or histamine conjugates having incorporated therewith a radioactive isotopic component are readily detected by radiation detecting devices. Paramagnetic materials bound to histamine are readily detected by NMR analysis. Fluorescent indicators and dyes are detected by their spectral properties, e.g. by a fluorometer.

Finally, the amount of histamine which reacted with the receptor is readily calculated by difference. For example, if 80 percent of the receptors were occupied by the histamine-indicator conjugate, 20 percent had been reacted with histamine. In a homogeneous assay system, the free histamine and histamine-indicator compete for receptors in proportion to their presence in the dispersion. In all cases, it is necessary to run an assay with histamine standards in the same manner as for the experimental assay.

It has been found that the enzymatic activity of alkaline phosphatase is enhanced when it is bound to histamine in a histamine-alkaline phosphatase indicator conjugate, which conjugate is bound to a receptor. This stimulation of enzyme activity is concentration dependent, is inhibitable by free histamine and occurs after the histamine-enzyme conjugate is bound to the receptor, either on whole cells, in solution or on a solid phase support. This stimulation effect has been confirmed as histamine receptor specific by showing that the enhanced activity of the enzyme is inhibited by adding histamine to the receptor preparation before incubation with histamine-alkaline phosphatase bound to a receptor.

Such a result is unusual, since linking an entity to an enzyme generally inhibits the activity of the enzyme, e.g., Emit® (Syva Co.). However, Rotman, M. B., et al., "Antibody-mediated activation of a defective β-D-galactosidase extracted from an *Escherichia coli* mutant," Proc. Natl. Acad. Sci. USA 60, 660 (1968) reported that an enzyme-ligand conjugate was stimulated when bound by an antibody. This latter conjugate was not bound to a receptor and is unique to a mutant bacterial source of β-D-galactosidase.

The histamine assay methods of the invention are useful in heterogeneous and homogeneous assay systems for utility in clinical and laboratory research applications. In a homogeneous phase assay, the amount of histamine-alkaline phosphatase bound to histamine receptors is quantitated on the basis of the stimulation of the enzyme kinetics that occurs upon such binding. Thus, one measures the enzymatic activity in a sample having both bound and unbound histamine-enzyme and compares this value to a standard curve established using known amounts of histamine.

This aspect of the invention provides the basis for an option of a homogeneous phase assay, rather than the conventional heterogeneous phase assay, in which the unbound histamine-alkaline phosphatase indicator is not removed from the sample being analyzed. Separation is not required in this homogeneous phase assay because the relative amounts of histamine-enzyme bound to histamine receptors are indicated by the relative amounts of stimulation of the enzyme kinetics.

Kits for competitive inhibition assays and enzyme stimulation assays are particularly useful for the determination of allergen sensitivity. The kit may contain various allergens or agents that induce the release of histamine from mast cells or basophils which are histamine-containing cells of animal origin.

When providing kits or articles by which the method of the invention may be practiced routinely, it is useful to provide components of the assay systems to the user. A kit for carrying out the method of the present invention may comprise in its simplest form (1) histamine receptors in an amount sufficient to provide an excess for binding with an amount of histamine in a sample to be assayed, and (2) a histamine-indicator conjugate in an amount sufficient to react with the resulting unbound histamine receptors present after reaction of the sample histamine with the histamine receptors.

The histamine receptors optionally may be bound to a particulate or continuous support. The kit may further comprise indicator substrate if appropriate, allergens, and histamine samples for generation of standard curves or results to be compared with experimental measurements. For example, a kit may contain a plurality of receptacles, such as test tubes or a microtiter plate. Individual receptacles may contain: histamine receptors (which may be attached to the inner surface of the receptacle in the case of a heterogeneous assay); the histamine-indicator conjugate plus appropriate buffering salts; a suitable substrate when an enzymatic or chemiluminescent indicator is used, and a reaction stopping reagent in a separate receptacle; precisely quantitated amounts of various suspected allergens where the kit is intended for use as an assay of clinical sensitivity towards an allergen; aliquots of known amounts of histamine to be used in establishing a standard curve; and some of the above-described receptacles may also contain premeasured amounts of an agent known to be sufficient to cause maximal release of the preformed histamine stores of basophils or mast cells. Optionally, the kit may further comprise histamine standards to be admixed with a portion of the histamine receptors and a portion of the histamine-indicator conjugate.

Objects and advantages of this invention are further illustrated by the following examples, but the particular materials and amounts thereof recited in these examples, as well as other conditions and details, should not be construed to unduly limit this invention.

EXAMPLE 1

Preparation of histamine receptors

A human T lymphoblastoid cell line, MOLT-4F, was grown by standard tissue culture techniques in RPMI 1640, glutamine, 10 percent heat-inactivated fetal calf sera and 100 units of Pen-Strep per ml at 37° C., 100 percent humidity and 5 percent carbon dioxide.

In order to free the histamine receptors from the cell wall, the cells were washed three times in phosphate buffered saline, resuspended at a concentration of $1 \times 10^7$ cells per ml in phosphate-buffered saline and either stored at 4° C. for three days or incubated at 46° C. for 90 minutes. The cells were then centrifuged at 1000 X G for ten minutes. The supernatant liquid containing the shed histamine receptors was removed by aspiration and the cell pellet discarded.

EXAMPLE 2

Attachment of histamine receptors to a solid support

Samples of 200 microliters of heat-inactivated fetal calf sera were added to each well of a polystyrene microtiter plate as a protein pretreatment and the seracontaining plates were incubated at 25° C. for 15 minutes. Each well was then washed twice with phosphate-buffered saline. To each well was added 200 microliters of 1 millimolar trinitrobenzene sulfonate in phosphate-buffered saline, and the plate was incubated at 37° C. for thirty minutes. Each well was then washed three times with phosphate-buffered saline. To each well was then added 200 microliters of histamine receptor in phosphate buffered saline prepared according to the procedure of EXAMPLE 1. The plate was then incubated at 25° C. for thirty minutes. After the incubation, each well was washed three times with phosphate-buffered saline and the plates were allowed to air dry at 25° C. for about 16 hours, then stored at 4° C.

EXAMPLE 3

Preparation of histamine-alkaline phosphatase conjugate

To a solution of $3.9 \times 10^{-3}$ mg of histamine hydrochloride in 10 ml of 0.01M phosphate buffered saline of pH 7.2 was added $5.6 \times 10^{-3}$ mg of 1-ethyl-3-(3-dimethylaminopropyl)carbodiimide hydrochloride in 10 ml of phosphate buffered saline. After mixing at 25° C. for thirty minutes, 10 mg of alkaline phosphatase Type III (Sigma) in 10 ml of phosphate buffered saline was added. The mixture was mixed gently at 25° C. for two hours, then dialyzed at 4° C. against phosphate-buffered saline. The dialysate was then chromatographed on a column of Sephadex® G-200 (Pharmacia, Sweden). The peak containing both histamine and enzymatic activity was separated and diluted to a concentration of 40 mg of protein per ml. This protein-containing material was the conjugate histamine-alkaline phosphatase.

EXAMPLE 4

Preparation of histamine-horseradish peroxidase conjugate

Part A

A solution of 5 mg histamine and 12 mg horseradish peroxidase in one milliliter of 0.1M aqueous phosphate buffer (pH 6.8) was prepared. To this stirred solution was added dropwise 0.05 ml of 1 percent aqueous glutaraldehyde solution and the solution was stirred for two hours. The resulting solution was dialyzed for 16 hours at 4° C. with two liters of phosphate-buffered saline solution. The dialysate was centrifuged for 30 minutes at 4° C. at 20,000 rpm to remove particulate matter and provide horseradish peroxidase-histamine conjugate. The stability of the conjugate was determined by storing a portion at 4° C. for 3 months. It was found to be verifiably stable.

Part B

Hydrogen peroxide for use as the enzyme substrate was prepared as follows: One milliliter of 30 percent hydrogen peroxide was diluted to a total volume of 100 ml with glass distilled water. One milliliter of this solution was further diluted with 50 ml of 0.2M potassium phosphate buffer (pH 7.0) to provide a concentration of 0.0017M hydrogen peroxide.

Part C

4-Aminoantipyrine for use as a spectrophotometrically detectable indicator was prepared as follows: A solution of 810 mg of phenol in 40 ml of water was prepared. To this solution was added 25 mg of 4-aminoantipyrine. The solution was then diluted to a total volume of 50 ml with water. The final concentration of 4-aminoantipyrine was 0.0025M.

Part D

To obtain reference graphs for the determination of histamine the following procedure was used:

To a microtiter plate coated with histamine receptor using the method of Example 2, was added, in triplicate, concentrations of zero (blank), 25, 50, 75 and 100 microgram per well of histamine. Each well was diluted to a final volume of 100 microliters with phosphate-buffered saline containing 0.05 percent Tween 20 surfactant. This solution was shaken at room temperature for 15 minutes and washed three times with phosphate-buffered saline.

To this solution was added 30 microliters of horseradish-peroxidase-histamine conjugate as prepared in Part A. Each of the wells was then diluted to a total volume of 100 microliters. The solutions were shaken for 30 minutes, then each well was emptied and washed three times with phosphate-buffered saline. All of the histamine receptors of each well had been reacted with either histamine or horseradish peroxidase-histamine conjugate.

To each well was then added 100 microliters of 0.0017M hydrogen peroxide solution and 100 microliters of 0.0025M 4-aminoantipyrine solution. The solutions were incubated for 10 minutes at 37° C. then the reaction was stopped by the addition of 1N aqueous sodium hydroxide solution. The replicates were pooled and the absorbance was read at 510 nm with a Beckman spectrophotometer. The results are shown below in TABLE I:

TABLE I

| Histamine Concentration (in micrograms) | Absorbance |
|---|---|
| 0 | .400 |
| 25 | .310 |
| 50 | .285 |
| 75 | .205 |
| 100 | .125 |
| Background | .095 |

In order to measure the histamine level in an unknown sample, wells of a microtiter plate coated with histamine receptors were reacted with a sample containing histamine, sequentially reacted with excess horseradish peroxidase-histamine conjugate, then hydrogen peroxide and 4-aminoantipyrine. Stopping the reaction with sodium hydroxide solution and measuring the absorbance provided a value which was compared to the above values and extrapolated to provide measurement of the concentration of histamine.

EXAMPLE 5

Human T lymphoblastoid cells, MOLT-4F, grown as described in EXAMPLE 1, were washed three times with phosphate-buffered saline and resuspended at $1 \times 10^6$ cells per ml in phosphate-buffered saline with 1 percent bovine serum albumin and 0.05 percent Tween 20. To 100 microliters of cells was added 10 microliters of a dilution of column-purified histamine-alkaline phosphatase conjugate prepared as described in Example 3. Samples using histamine-enzyme dilutions of 1:2, 1:4, 1:8 and 1:16 were used. The samples were incubated for thirty minutes at 37° C., then centrifuged at 1000 X G, and the cell pellet was separated and resuspended in 1 ml of aqueous para-nitrophenyl phosphate solution, containing 1 mg per ml p-nitrophenyl phosphate in a buffer of pH 9.8 having the composition: 0.05M sodium carbonate, 0.9 weight percent sodium chloride, and 1 millimole magnesium chloride. The suspension was incubated for one hour at 37° C., then 100 microliters of 1N aqueous sodium hydroxide solution was added to stop the enzymatic reaction. The samples were centrifuged at 1000 X G for 10 minutes, the supernatant was decanted and the absorbance of the supernatant at $A_{410}$ (absorbance at 410 nm) read on a Beckman spectrophotometer to determine the amount of product formed. The results are shown in TABLE II:

TABLE II

| Dilution of Histamine-alkaline phosphatase | $A_{410}$ of Supernatant |
|---|---|
| Undiluted | 0.290 |
| 1:2 | 0.133 |
| 1:4 | 0.087 |
| 1:8 | 0.058 |
| 1:16 | 0.042 |

EXAMPLE 6

Demonstration of sensitivity of the assay

To determine the sensitivity of the histamine assay, an inhibition assay was performed using whole cells with histamine in 0.01M phosphate-buffered saline as the inhibitor. The histamine was incubated with $1 \times 10^6$ cells for 30 minutes. The unbound inhibitor was washed out and the histamine-enzyme added and incubated 30 minutes. After washing out the unbound indicator, the enzyme substrate, p-nitrophenyl phosphate was added and incubated for 1 hour at 37° C. The enzymatic reaction was stopped with 1N aqueous sodium hydroxide and the absorbance at A410 read from a Beckman spectrophotometer. The amount of product formed was inversely proportional to the amount of free histamine bound to the cells. The results of this inhibition assay are presented in TABLE III which illustrates that clinically significant ng levels of histamine are detected.

TABLE III

Histamine Inhibition of Histamine-Enzyme Binding to Whole Cells

| Histamine added | Percent inhibition of enzyme activity |
|---|---|
| 50 g | 69 |
| 5 g | 45 |
| 500 ng | 32 |
| 50 ng | 24 |
| 5 ng | 14 |
| 500 pg | 7 |

EXAMPLE 7

Demonstration of sensitivity of the assay with receptor on a solid support

Cell surface histamine receptors prepared as described in EXAMPLE 1 were affixed to microtiter plate wells by protein pretreatment (see EXAMPLE 2) of the plate followed by surface activation with 1 millimolar trinitrobenzene sulfonate as described in EXAMPLE 2.

An inhibition assay was carried out to demonstrate the sensitivity of the assay using receptors attached to a solid support. The various quantities of histamine in phosphate-buffered saline were incubated in several replications with the receptor. After washing the plates with phosphate-buffered saline, histamine-alkaline phosphatase indicator was added and incubated for 30 minutes. After washing out the unbound indicator, para-nitrophenyl phosphate was added and incubated for 1 hour at 37° C. The enzymatic reaction was stopped with 1N aqueous sodium hydroxide and the absorbance at $A_{410}$ read from a Beckman spectrophotometer. The results shown in the table indicate an assay sensitivity of less than 1 nanogram of histamine per sample.

TABLE IV

Histamine Inhibition of Histamine-Enzyme Binding to Receptors Attached to a Solid Phase

| ng Histamine added | Percent inhibition of enzyme activity |
|---|---|
| 25 | 79 |
| 10 | 72 |
| 5 | 65 |
| 1 | 60 |
| 0.5 | 52 |
| 0.25 | 46 |
| 0.1 | 40 |
| 0.05 | 30 |

EXAMPLE 8

Demonstration of sensitivity of the assay to histamine in the presence of blood

Using the method described in EXAMPLES 6 and 7, the sensitivity of the assay to histamine dissolved in anticoagulated human whole blood was measured. The data of TABLE V illustrates that the sensitivity of the assay was acceptable at levels of 1 nanogram of histamine per sample.

TABLE V

Histamine in whole blood: inhibition of histamine-enzyme binding to receptors attached to a solid phase

| ng Histamine added | Percent inhibition of enzyme activity |
|---|---|
| 25 | 91 |
| 10 | 79 |
| 5 | 70 |
| 1 | 49 |

EXAMPLE 9

Receptor bound histamine-enzyme stimulation after binding to whole cells

Ten microliters of histamine alkaline phosphatase were incubated with $1 \times 10^6$ cells for 30 minutes, the unbound indicator was then washed out and the cells were incubated with the enzyme substrate, paranitrophenyl phosphate, for 60 minutes. The reaction was stopped with 1N aqueous sodium hydroxide and the product formed was quantified spectrophotometrically. The total enzyme activity was determined by incubating 10 microliters of the dilutions of histamine-enzyme with the enzyme substrate for 60 minutes, stopping the reaction with 1N aqueous sodium hydroxide and quantifying the product formed. The data is shown in TABLE VI.

TABLE VI

Stimulation of histamine-enzyme activity after binding to whole cells

| Dilution of histamine-enzyme | Percent stimulation of total enzyme activity after binding to cells |
|---|---|
| — | 9 |
| 1:2 | 8 |
| 1:4 | 24 |
| 1:8 | 54 |
| 1:16 | 116 |

| Dilution of histamine-enzyme | Percent of total enzyme activity after binding to cells |
|---|---|
| 1:32 | 190 |
| 1:64 | 483 |
| 1:128 | 757 |
| 1:256 | 1441 |

To determine if the stimulation of the histamine-enzyme after binding to the receptor was due to specific binding of the histamine moiety, an inhibition assay was performed as described in EXAMPLE 9. Histamine conjugated to bovine serum albumin in phosphate-buffered saline was used as the inhibitor and a 1:128 dilution of histamine-enzyme was used as the indicator. The results in TABLE VII illustrate that the stimulation was indeed inhibitable by free histamine and thus was specific for histamine.

TABLE VII

Histamine inhibition of histamine-enzyme binding to whole cells

| Histamine-bovine serum albumin | Percent inhibition of enzyme activity |
|---|---|
| 60 μg | 67 |
| 6 μg | 64 |
| 600 ng | 45 |
| 60 ng | 35 |
| 6 ng | 26 |

EXAMPLE 10

Stimulation of the enzyme kinetics of histamine-alkaline phosphatase upon binding to a soluble histamine receptor A conjugate of histamine-alkaline phosphatase prepared at a 1:1 ratio according to the method of EXAMPLE 3 was used at a concentration of 2 mg/ml. Histamine receptors were prepared by the heat shock release method from MOLT-4F cells according to the method of EXAMPLE 1. The receptor preparation was lyophilyzed and stored at $-20°$ C. A 0.1 ml portion of reconstituted (phosphate-buffered saline) receptor was added to 0.1 ml of histamine-alkaline phosphatase in enzyme buffer. Further receptor dilutions were prepared as indicated in TABLE VIII. After five minutes incubation at 25° C., 1 ml of enzyme substrate, para-nitrophenyl phosphate, was added. The sample was then monitored for increase in $A_{410}$ in a recording spectrophotometer. The results are given in TABLE VIII as relative slopes of the increase in absorbance over time.

TABLE VIII

| Dilutions, receptor:buffer | Slope | Percent increase in slope |
| --- | --- | --- |
| — | 62.5 | — |
| 1:1 | 76.0 | 21.6 |
| 1:2 | 72.0 | 15.3 |
| 1:4 | 65.5 | 4.8 |
| 1:8 | 65.0 | 4.0 |
| 1:16 | 61.0 | 0 |

The data in TABLE VIII show that as increasing proportions of a given amount of histamine-enzyme conjugate were bound by receptors, the kinetic activity of the enzyme-catalyzed reaction was increased. Binding of the histamine portion of the conjugate resulted in stimulation of the kinetic activity of the enzyme.

EXAMPLE 11

Radioactive histamine as the histamine-indicator.

A solution of 2,5-$^3$H-histamine hydrochloride in water was prepared using labeled histamine with a specific activity of 9 Curies per mmole and a concentration of 1 micro-Curie per microliter. This $^3$H-labeled-histamine was then diluted 50 to 1 with phosphate-buffered saline containing 1 percent bovine serum albumin and 0.05 percent Tween 20.

This solution (200 microliters per well) was placed in the wells of a microtiter plate. Each well contained histamine receptor prepared as described in EXAMPLE 2. The solution was incubated for 60 minutes at 37° C. then the wells were washed with phosphate-buffered saline containing 1 percent bovine serum albumin and 0.05 percent Tween 20 in order to remove unbound material.

In order to demonstrate that the $^3$H-labeled histamine could be used as an indicator it was extracted from the wells using two portions of methanol. The radioactivity of the methanol washes was then counted in Aquasol ® (New England Nuclear) using a Beckman scintillation counter. The results are shown in TABLE IX below:

TABLE IX

| Sample | Average $^3$H Counts per minute |
| --- | --- |
| Receptor wells | 7968 |
| Control wells | 1172 |

The data of TABLE IX show that radioactivity counts must be corrected for nonspecific binding. Further, Example 11 shows that the indicator system of the present example can be used to determine histamine concentration in a sample.

EXAMPLE 12

Fluorescent dye labeled histamine as the histamine indicator

A sample of rhodamine, a fluorescent dye, was reacted with histamine to provide dye-labeled histamine indicator. This indicator was reacted with the histamine receptor on whole cells in solution in order to determine if the histamine-indicator binding would be specific for histamine. This reaction was carried out as a competitive reaction as described below:

Histamine was reacted with bovine serum albumin to provide a conjugate of histamine-bovine serum albumin. To 50 microliters of this conjugate at a concentration of 1.64 mg per ml of phosphate-buffered saline was added 100 microliters of human T lymphoblastoid cells, MOLT-4F, at a concentration of $1 \times 10^7$ cells per ml of phosphate-buffered saline containing 1 percent bovine serum albumin and 0.05 percent Tween 20. The mixture was incubated at 37° C. for 30 minutes. The cells were then washed three times with phosphate-buffered saline and resuspended in 100 microliters of phosphate-buffered saline containing 1 percent bovine serum albumin and 0.05 percent Tween 20. To this suspension was added 50 microliters of histamine-rhodamine indicator and the suspension was incubated for 30 minutes at 37° C. The suspension was then centrifuged at 1000X G for ten minutes. The supernatant liquid was removed by aspiration and the cell pellet was separated. The cell pellet was resuspended in 100 microliters of phosphate-buffered saline containing 1 percent bovine serum albumin and 0.05 percent Tween 20. The presence of histamine specific cell bound indicator was determined by fluorescence microscopy and the results are shown in TABLE X:

TABLE X

| Indicator | Fluorescence without histamine-bovine serum albumin (incubated with buffer only) | Fluorescence with histamine-bovine serum albumin conjugate |
| --- | --- | --- |
| histamine-rhodamine | Yes | No |
| bovine serum albumin-rhodamine | No | No |
| buffer | No | No |

We claim:

1. A method for determining the amount of histamine in a liquid test sample using histamine receptors and a histamine-indicator conjugate comprising the steps of:
   a. contacting a measured amount of said test sample with an excess of substantially Purified histamine receptors which are free in solution or bound to a continuous solid phase support,
   b. incubating and reacting said test sample with said histamine receptors, which reaction leaves unbound histamine receptors available for further bonding,
   c. contacting an amount of histamine-indicator conjugate with the bound and unbound histamine receptors sufficient to bind said conjugate to all unbound histamine receptors, d. incubating and reacting said histamine-indicator conjugate with said unbound histamine receptors, e. removing unbound histamine-indicator conjugate if necessary to measure the amount of histamine-indicator conjugate bound to said histamine receptors, f. measuring the amount of histamine-indicator conjugate bound to the histamine receptors, and g. determining the amount of histamine in said test sample by comparison with standard curves, with the proviso that said histamine-indicator conjugate maintains its activity or undergoes stimulation of activity when bound to said histamine receptors, and said method being capable of measuring at least 0.05 ng of histamine in a test sample.

2. The method according to claim 1 wherein said test sample and said histamine-indicator conjugate are simultaneously contacted and incubated with said histamine receptors.

3. The method according to claim 1 wherein said histamine-indicator conjugate is a histamine-enzyme conjugate.

4. The method according to claim 3 wherein the indicator of said histamine-indicator conjugate is alkaline phosphatase or horseradish peroxidase.

5. The method according to claim 1 wherein the source of histamine receptors is mammalian cells.

6. The method according to claim 1 wherein the source of histamine receptors is human lymphoid cells in culture.

7. The method according to claim 1 wherein the source of histamine receptors is lymphoid cells grown in suspension.

8. The method according to claim 1 wherein the source of histamine receptors is mammalian and the histamine-indicator conjugate is a histamine-enzyme conjugate.

9. The method according to claim 1 wherein more than 5 percent but less than 95 percent of the receptors have been reacted with histamine.

10. The method according to claim 1 wherein less than 95 percent but more than 5 percent of the receptors have been reacted with a histamine-indicator conjugate.

11. The method according to claim 1 wherein said histamine receptors are bound to cells.

12. A kit for use in the histamine assay method of claim 1 comprising (a) substantially purified histamine receptors which are free in solution or bound to a continuous solid phase support in an amount in excess of the amount required to bind all of the histamine in a test sample, and (b) a histamine-indicator conjugate in an amount sufficient to react with all unbound histamine receptors remaining after reaction of the test sample with said histamine receptors, said histamine-indicator conjugate maintains its activity or undergoes stimulation of activity when bound to said histamine receptors, and said kit being capable of measuring at least 0.05 ng of histamine in a test sample.

13. The kit according to claim 12 further comprising histamine standards to be admixed with a portion of said histamine receptors and subsequently or simultaneously with a portion of said histamine indicator conjugate.

14. The kit according to claim 12 useful in an enzyme stimulation assay method for the determination of histamine wherein said receptors are free in solution or are bound to (a) cells or (b) solid surfaces.

15. The kit according to claim 12 further comprising an amount of an allergen sufficient to stimulate histamine release from basophils or mast cells from an allergically sensitive mammal, said allergen being incorporated with said histamine receptors.

16. A method for determining the amount of histamine in a liquid test sample using histamine receptors and histamine-alkaline phosphates as a histamine-indicator conjugate comprising the steps of:

a. contacting a measured amount of said test sample with an excess of substantially purified histamine receptors which are free in solution or bound to a continuous solid phase support, b. incubating and reacting said test sample with said histamine receptors, which reaction leaves unbound histamine receptors available for further bonding, c. contacting an amount of histamine-alkaline phosphatase with the bound and unbound histamine receptors sufficient to bind said conjugate to all unbound histamine receptors, d. incubating and reacting said histamine-alkaline phosphatase with said unbound histamine receptors, e. removing unbound histamine-alkaline phosphatase if necessary to measure the amount of histamine-alkaline phosphatase bound to said histamine receptors, f. measuring the amount of histamine-alkaline phosphatase bound to the histamine receptors, and g. determining the amount of histamine in said test sample by comparison with standard curves, with the proviso that said histamine-alkaline phosphatase undergoes stimulation of activity when bound to said histamine receptors, and said method being capable of measuring at least 0.05 ng of histamine in a test sample.

* * * * *

UNITED STATES PATENT AND TRADEMARK OFFICE
CERTIFICATE OF CORRECTION

PATENT NO. : 4,544,629

DATED : October 1, 1985

INVENTOR(S) : Thomas K. Rice and Therese A. Senta

It is certified that error appears in the above-identified patent and that said Letters Patent is hereby corrected as shown below:

```
Column 11, line 15 (TABLE III), delete "50 g" (under
Histamine added column) and insert --50 µg-- therefor Column 11, line 16, (TABLE III), delete "5 g" (under
Histamine added column) and insert --5 µg-- therefor
```

Signed and Sealed this

Eleventh Day of February 1986

[SEAL]

Attest:

DONALD J. QUIGG

Attesting Officer

Commissioner of Patents and Trademarks